US008857282B2

(12) United States Patent
Lee-Smith

(10) Patent No.: US 8,857,282 B2
(45) Date of Patent: Oct. 14, 2014

(54) METHOD AND SAMPLE HOLDING ASSEMBLY FOR USE IN SAMPLE PREPARATION

(75) Inventor: Roger Lee-Smith, Suffolk (GB)

(73) Assignee: Genevac Limited, Suffolk (GB)

( * ) Notice: Subject to any disclaimer, the term of this patent is extended or adjusted under 35 U.S.C. 154(b) by 324 days.

(21) Appl. No.: 13/254,465

(22) PCT Filed: Mar. 29, 2010

(86) PCT No.: PCT/GB2010/050523
§ 371 (c)(1),
(2), (4) Date: Oct. 3, 2011

(87) PCT Pub. No.: WO2010/112902
PCT Pub. Date: Oct. 7, 2010

(65) Prior Publication Data
US 2012/0011945 A1 Jan. 19, 2012

(30) Foreign Application Priority Data
Mar. 31, 2009 (GB) .................................. 0905450.3

(51) Int. Cl.
*B01L 3/00* (2006.01)
*G01N 1/40* (2006.01)
(52) U.S. Cl.
CPC ........... *B01L 3/508* (2013.01); *B01L 2200/026* (2013.01); *B01L 2200/0678* (2013.01); *B01L 2200/04* (2013.01); *G01N 2001/4027* (2013.01)
USPC ...................................................... 73/864.91
(58) Field of Classification Search
CPC ........... G01N 1/40; B01D 11/407; B01L 3/00
USPC .............................. 73/863.21, 863.42, 864.31
See application file for complete search history.

(56) References Cited

U.S. PATENT DOCUMENTS 3,897,902 A * 8/1975 Yanez, Jr. .......................... 494/10
4,376,391 A * 3/1983 Brunnee ...................... 73/863.12
(Continued)

FOREIGN PATENT DOCUMENTS

| DE | 199 38 946 A1 | 3/2001 |
|---|---|---|
| EP | 1 477 812 A2 | 11/2004 |

(Continued)

OTHER PUBLICATIONS

European Patent Office, International Search Report and Written Opinion of the International Searching Authority, International Application No. PCT/GB2010/050523, mailed Jun. 8, 2010 (10 pages).

*Primary Examiner* — Hezron E Williams
*Assistant Examiner* — Mark A Shabman
(74) *Attorney, Agent, or Firm* — Wood, Herron & Evans, LLP

(57) ABSTRACT

A method and sample holding assembly are described for use in the preparation of samples for analysis. The method comprises the steps of collecting a sample in a concentration tube which is open at one end and closed at the other, the closed end being selectively openable. A vial is coupled to the open end, the tube is inverted, the closed end is opened, and then solvent is evaporated from the sample via the opened end until the concentrated sample is confined to the vial. A sample holding assembly for use in the present method is also described. It comprises a concentration tube, and an adaptor arrangement for coupling a vial to the open end of the tube and defining a fluid path between the tube and the vial.

11 Claims, 2 Drawing Sheets

(56) References Cited

U.S. PATENT DOCUMENTS

| | | | |
|---|---|---|---|
| 4,755,301 A * | 7/1988 | Bowers | 210/650 |
| 5,022,967 A * | 6/1991 | Stieg | 202/197 |
| 5,958,778 A * | 9/1999 | Kidd | 436/45 |
| 5,998,217 A * | 12/1999 | Rao et al. | 436/179 |
| 6,682,631 B2 * | 1/2004 | Cole | 159/6.1 |
| 6,749,755 B2 * | 6/2004 | Johnson | 210/650 |
| 2003/0222007 A1 * | 12/2003 | Gu et al. | 210/198.2 |
| 2005/0258097 A1 * | 11/2005 | Gjerde et al. | 210/635 |
| 2006/0063268 A1 * | 3/2006 | Prest | 436/86 |
| 2006/0124551 A1 * | 6/2006 | Gjerde et al. | 210/656 |
| 2007/0026380 A1 * | 2/2007 | Johnson et al. | 435/4 |
| 2007/0224089 A1 * | 9/2007 | Logan | 422/102 |
| 2010/0218594 A1 * | 9/2010 | Johnson et al. | 73/23.41 |

FOREIGN PATENT DOCUMENTS

| | | | | |
|---|---|---|---|---|
| EP | 1 640 701 A2 | 3/2006 | | |
| GB | 2 436 075 A | 9/2007 | | |
| WO | 01/04600 A1 | 1/2001 | | |
| WO | 02/066134 A1 | 8/2002 | | |
| WO | WO 2004039471 A1 * | 5/2004 | | B01D 1/22 |
| WO | 2007/130991 A1 | 11/2007 | | |
| WO | WO 2007130991 A1 * | 11/2007 | | |

\* cited by examiner

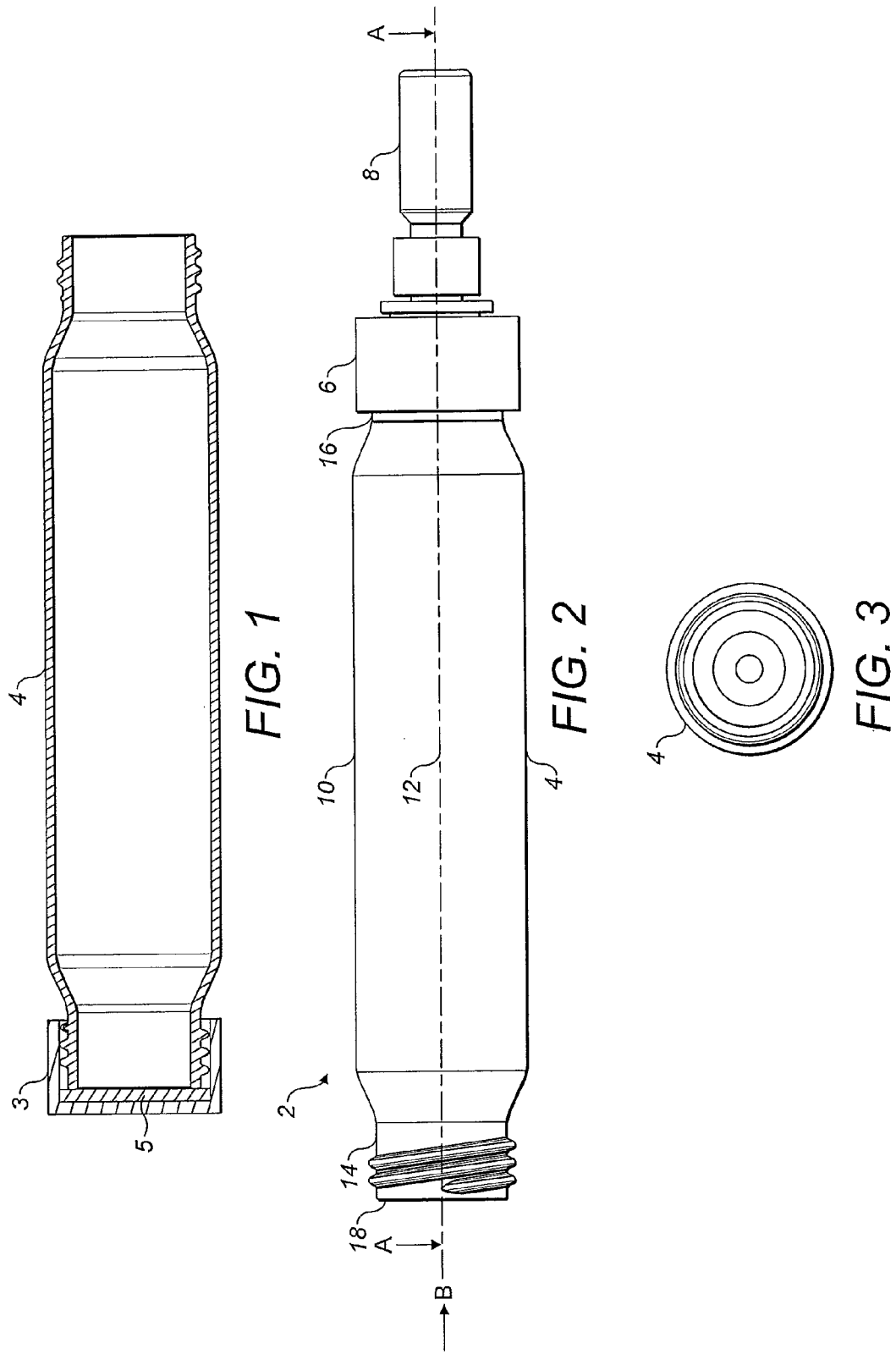

METHOD AND SAMPLE HOLDING ASSEMBLY FOR USE IN SAMPLE PREPARATION

CROSS-REFERENCE TO RELATED APPLICATION

This application is a submission under 35 U.S.C. §371 of International Application No. PCT/GB2010/050523, filed Mar. 29, 2010, which claims priority to Great Britain Application No. 0905450.3, filed Mar. 31, 2009, the disclosures of which are hereby expressly incorporated by reference herein in their entireties.

FIELD OF THE INVENTION

The present invention relates to preparation of samples for analysis in which the samples comprise at least one solute dissolved in a solvent.

BACKGROUND TO THE INVENTION

In order to prepare samples for analysis, it is often necessary to obtain a concentrated solution held within a vial compatible with the analysis apparatus. For example, a solvent extraction system may typically provide a sample consisting of a mixture of solutes dissolved in a solvent having a volume of around 40 ml or more. The sample then needs to be concentrated to a significantly smaller volume for further analysis. This concentration process may be carried out by a centrifugal evaporator, for example. The sample volume may typically be reduced to around 0.5 ml.

The concentrated solution is then transferred to a vial compatible with the analysis apparatus. This transfer is carried out manually using a pipette. This inevitably involves some loss of the concentrated sample and risks cross-contamination. Furthermore it is a slow process which needs to be carried out with great care.

It is known to provide an evaporation flask having a vial coupled to an opening in its base so that a sample can be concentrated directly into a vial (as in the SampleGenie products commercially available from Genevac Limited, the common assignee). However, where the original sample is collected in apparatus employing relatively small containers, it is impractical to replace that container by a flask and vial combination due to the limited space available in the collection apparatus for the container.

SUMMARY OF THE INVENTION

The present invention provides a method of preparing a sample for analysis, wherein the sample comprises at least one solute in a solvent, comprising the steps of:
 providing the sample in a concentration tube which is open at one end and closed at the other, the closed end being selectively openable;
 coupling a vial to the one end;
 inverting the tube;
 opening the other end of the tube; and
 evaporating solvent from the sample via the other end of the tube, until the concentrated sample is confined to the vial.

Accordingly, the sample is initially collected in the concentration tube, the dimensions of the concentration tube being compatible with the system creating the sample. The sample in the concentration tube can then be readily and reliably prepared for concentration directly into a vial by coupling the vial to the open end of the tube and inverting the tube. The assembly comprising the concentration tube and vial can be loaded into an evaporator, allowing the sample to be concentrated into the vial for further processing.

Thus, the vial may be decoupled from the tube after the evaporation step and loaded into analysis apparatus, such as chromatographic analysis apparatus. More particularly, the analysis apparatus may be a gas chromatography system and the vial a gas chromatography vial compatible with such a system.

The present invention further provides a sample holding assembly comprising:
 a concentration tube which is open at one end and closed at the other, the closed end being selectively openable; and
 an adaptor arrangement for coupling the vial to the open end of the tube and defining a fluid path therebetween.

The adaptor arrangement may advantageously comprise an adaptor having a tube end for coupling to the tube and a vial end for coupling to a vial, and a container (or other retaining device) for receiving a vial, the container being arranged to couple with the vial end of the adaptor such that the open end of the vial is held in fluid communication with the fluid path through the adaptor.

More particularly, the container and adaptor are coupled together by complementary screw threads, and the adaptor arrangement includes a seal configured such that as the container is screwed onto the adaptor, the open end of a vial held in the container is urged against the seal.

Preferably, the other, closed end of the concentration tube is closed by a removable cap, or a closure having a fluid path therethrough which is selectively openable to allow evaporated solvent to escape via that end of the tube.

In a preferred embodiment, the removable cap and tube are coupled together by complementary screw threads. Similarly, the adaptor and tube may be coupled together by complementary screw threads. In particular, the screw threads at each end of the tube may be of substantially the same pitch.

BRIEF DESCRIPTION OF THE DRAWINGS

Sample holding assemblies embodying the present invention will now be described by way of example with reference the accompanying drawings, wherein:
FIG. 1 is a cross-sectional side view of a concentration tube and cap;
FIG. 2 is a side view of the concentration tube with a vial coupled to one end;
FIG. 3 an end view in direction B of the assembly of FIG. 2.

DETAILED DESCRIPTION OF THE INVENTION

FIG. 1 shows a concentration tube 4 and an associated end closure in the form of cap 3. A fluid-tight seal between the tube and cap is provided in the form of a seal 5. The seal is formed of an inert deformable material, such as PTFE for example.

Figure 4:
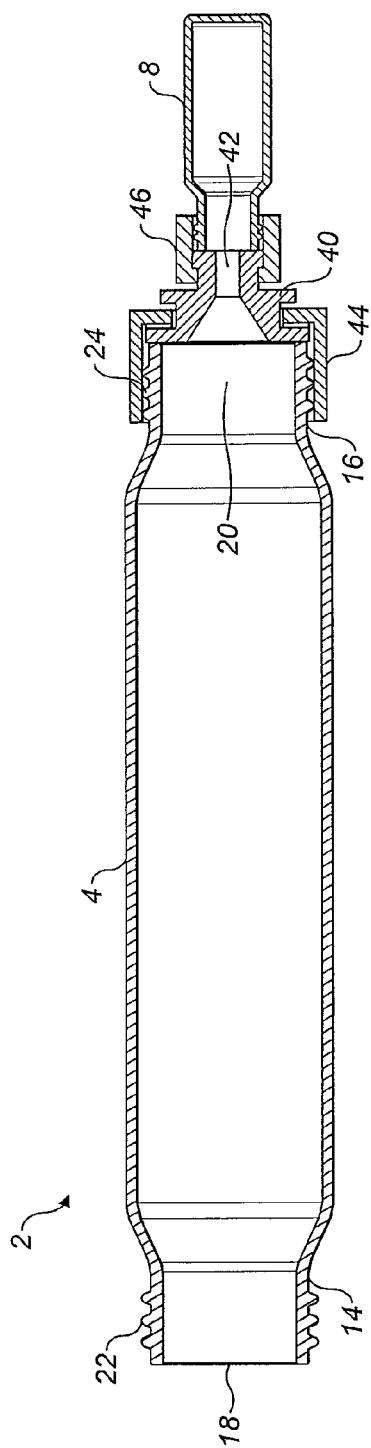
FIG. 4 is a cross-sectional side view along line A-A of the assembly of FIG. 2.

The sample holding assembly 2 shown in FIGS. 2 to 4 comprises a concentration tube 4, and an adaptor 6, and a concentration vial 8 (a cap 3 is omitted from these Figures).

The concentration tube 4 has a cylindrical mid-section and a central, longitudinal axis 12. It also includes cylindrical end sections 14 and 16 having a smaller diameter than the mid-section. For example, in a concentration tube having a volume of around 40 ml, the mid-section has a diameter of around 27.5 mm, and a length of around 140 mm, with the diameter of the end sections 14, 16 being around 17 mm. Each end section defines a respective opening 18, 20 at opposite ends of the tube 4. A screw thread 22, 24 is formed on the outer circumferential surface of each end section 14, 16 respectively. The threads are of equal pitch, but different threads could instead be provided at each end. The tube is formed of borosilicate glass, for example.

The dimensions of the concentration tube are such that it is compatible with an extraction system used to collect the sample to be analysed. An example of such an extraction system is the Accelerated Solvent Extraction (ASE) system marketed by Dionex.

The vial 8 may be a gas chromatography vial. Common dimensions for such a vial are a diameter of 12 mm and a length of 32 mm.

Vial 8 is coupled to the opening 20 of the concentration tube by adaptor 6. As can be seen in FIG. 4, the adaptor consists of a connector 40 which defines a fluid path 42 along its central axis to allow fluid to flow between the concentration tube and the vial. Connector 40 is held against the open end 20 of the concentration tube by a threaded coupling 44 which engages the thread 24 on the tube. A second coupling 46 holds the connector 40 against the open end of the vial 8 by screwing onto a thread defined around the open neck of the vial. The components of the adaptor may be formed of polypropylene, PTFE, or another inert polymer for example.

Figure 5:
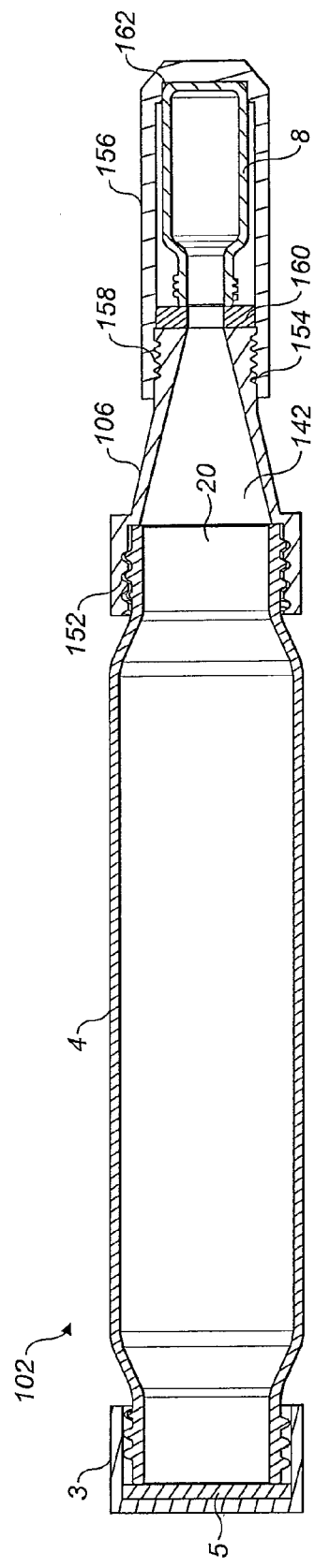
FIG. 5 is a cross-sectional side view of another embodiment of a sample holding assembly.

FIG. 5 shows a sample holding assembly 102 similar to that of FIGS. 2 to 4. It illustrates an alternative way to fasten the vial 8 to the concentration tube 4.

Vial 8 is coupled to the opening 20 of concentration tube 4 by an adaptor 106. The adaptor defines a fluid path 142 along its central axis between the vial and the tube. It includes a screw thread 152 on an inner surface at one end for connection to thread 24 on the tube, and a further screw thread 154 on an outer surface at the other end.

A container 156 in the form of a cylinder closed at one end is configured to receive and contain vial 8 and closely fit around its base. An inner surface 162 of the closed end of the container is profiled so as to complement the circumferential region at the base of the vial and retain it in a central location within the container. The open end of the container defines a thread 158 on its inner surface for engagement with thread 154 of the adaptor 106. An O-ring seal 160 is held between the adaptor 106 and the open end of the vial 8.

As container 156 (with vial 8 held inside) is screwed onto adaptor 106, the vial is urged against the seal 160 so as to form a fluid-tight seal between vial and adaptor.

The adaptor and container configuration of FIG. 5 is particularly beneficial when it is desirable to insulate the vial to some extent during the concentration process. This may be the case for example when using a condensing evaporator (of the form described in a United Kingdom patent application published under No. 2436075 and filed by the common assignee). The insulation provided by the container serves to slow down the evaporation process allowing close control of the end point to avoid drying out the sample completely.

Use of a sample holding assembly of the form shown in the drawings in a method of preparing a sample for analysis will now be described. Initially, a concentration tube 4 with one end closed by a cap 3 is inserted into the extraction system and the sample collected in the tube. The tube containing the sample is removed from the extraction system and an adaptor 6 and vial 8 coupled to the open end of the tube. The tube is then inverted so that the sample flows into the concentration vial 8, with the remainder in the end of the tube connected to the vial.

The cap 3 is then removed, before loading the assembly into a concentrator such as a centrifugal evaporator. In the concentrator, solvent is evaporated from the sample via the open end 18 of the tube such that the sample is concentrated directly into the vial 8.

It would generally be impractical to provide a concentration tube, vial and adaptor for loading directly into an extraction system as this would lead to unacceptable reduction in the volume of sample that may be collected due to the limited space available. According to the present invention, the concentration tube alone is loaded into the extraction system whilst still allowing for reliable and efficient production of a concentrated sample in a separate vial.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of Applicant's invention.

What is claimed is:

1. A method of preparing a sample for analysis, wherein the sample comprises at least one solute in a solvent, using a concentration tube having first and second ends, the tube being open at the first end and closed at the second end, the second end being selectively openable, the method comprising the steps of:
   inserting the first end of the concentration tube into a sample extraction system, with the second end being closed, and collecting a sample in the tube;
   coupling a vial to the first end of the tube;
   inverting the tube;
   opening the second end of the tube; and
   evaporating solvent from the sample via the second end of the tube, until the concentrated sample is confined to the vial.

2. A method of claim 1, including the steps of decoupling the vial from the tube after the evaporation step, and loading the vial into analysis apparatus.

3. A method of claim 2, wherein the analysis apparatus is chromatographic analysis apparatus.

4. A method of claim 1, wherein the vial is a gas chromatography vial.

5. A method of claim 1, wherein the coupling step comprises coupling the vial to the first end of the tube with an adaptor arrangement which defines a fluid path between the tube and the vial.

6. A method of claim 5, wherein the adaptor arrangement comprises an adaptor having a tube end for coupling to the tube and a vial end for coupling to a vial, and a container for receiving a vial, the container being coupled with the vial end of the adaptor in the coupling step such that the open end of the vial is held in fluid communication with the fluid path through the adaptor arrangement.

7. A method of claim 6, wherein the container and adaptor are coupled together by complementary screw threads, and the adaptor arrangement includes a seal configured so that as the container is screwed onto the adaptor, the open end of the vial held in the container is urged against the seal.

8. A method of claim 5, wherein the adaptor and tube are coupled together by complementary screw threads.

9. A method of claim 5, wherein the sample extraction system comprises a solvent extraction system.

10. A method of claim 1, wherein the other end of the tube is closed by a removable cap and opened in the opening step by removing the cap.

11. A method of claim 10, wherein the removable cap and tube are coupled together by complementary screw threads.

* * * * *